(12) United States Patent
Florio et al.

(10) Patent No.: US 9,714,929 B2
(45) Date of Patent: Jul. 25, 2017

(54) METHOD TO CLASSIFY AND SELECT PROPPANTS

(71) Applicant: Halliburton Energy Services, Inc., Houston, TX (US)

(72) Inventors: Steven Florio, Houston, TX (US); Christopher E. Coker, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 627 days.

(21) Appl. No.: 14/228,275

(22) Filed: Mar. 28, 2014

(65) Prior Publication Data

US 2014/0290349 A1    Oct. 2, 2014

Related U.S. Application Data

(60) Provisional application No. 61/807,518, filed on Apr. 2, 2013.

(51) Int. Cl.
*B07C 5/34* (2006.01)
*G01N 33/24* (2006.01)
*E21B 43/267* (2006.01)

(52) U.S. Cl.
CPC .............. *G01N 33/24* (2013.01); *B07C 5/34* (2013.01); *E21B 43/267* (2013.01)

(58) Field of Classification Search
CPC  G01N 33/24; B07C 5/34; E21B 41/00; E21B 43/267
USPC .......................................... 166/280.1, 280.2
See application file for complete search history.

(56) References Cited

U.S. PATENT DOCUMENTS

| | | | |
|---|---|---|---|
| 3,496,765 A | 2/1970 | Rathmell | |
| 4,006,626 A | 2/1977 | Ruzicka et al. | |
| 4,289,023 A * | 9/1981 | Rader | E21B 47/0005 73/12.09 |
| 5,245,862 A | 9/1993 | Zeiss | |
| 5,852,587 A * | 12/1998 | Kostek | G01V 1/46 175/50 |
| 6,643,221 B1 * | 11/2003 | Hsu | G01V 1/523 166/249 |
| 6,892,887 B2 * | 5/2005 | Rayborn | B03B 5/04 209/17 |
| 7,459,209 B2 | 12/2008 | Smith et al. | |
| 7,491,444 B2 | 2/2009 | Smith et al. | |
| 7,533,775 B2 | 5/2009 | King et al. | |
| 7,569,199 B1 | 8/2009 | Barron et al. | |
| 7,867,613 B2 | 1/2011 | Smith et al. | |
| 7,883,773 B2 | 2/2011 | Smith et al. | |
| 7,887,918 B2 | 2/2011 | Smith et al. | |
| 7,914,892 B2 | 3/2011 | Smith et al. | |
| 8,003,212 B2 | 8/2011 | Smith et al. | |
| 8,012,533 B2 | 9/2011 | Smith et al. | |
| 8,047,288 B2 | 11/2011 | Skala et al. | |
| 8,075,997 B2 | 12/2011 | Smith et al. | |
| 8,168,570 B2 | 5/2012 | Barron et al. | |
| 8,178,476 B2 | 5/2012 | Xie et al. | |
| 8,178,477 B2 | 5/2012 | Skala et al. | |
| 8,298,667 B2 | 10/2012 | Smith et al. | |
| 8,603,578 B2 | 12/2013 | Smith et al. | |
| 2010/0197532 A1 * | 8/2010 | Rush | B02C 17/002 507/269 |
| 2011/0143969 A1 | 6/2011 | Skala | |
| 2011/0160104 A1 | 6/2011 | Wu et al. | |
| 2012/0157358 A1 | 6/2012 | Fang et al. | |
| 2012/0181020 A1 | 7/2012 | Barron et al. | |
| 2012/0190597 A1 | 7/2012 | Chatterjee et al. | |
| 2013/0014945 A1 | 1/2013 | Fang et al. | |
| 2013/0206408 A1 | 8/2013 | Chatterjee et al. | |
| 2013/0244914 A1 | 9/2013 | Wu et al. | |
| 2014/0038859 A1 | 2/2014 | Skala et al. | |
| 2014/0038860 A1 | 2/2014 | Skala et al. | |
| 2014/0190693 A1 * | 7/2014 | Johnson, Sr. | C09K 8/032 166/280.1 |
| 2016/0139588 A1 * | 5/2016 | Huang | G05B 19/406 700/275 |
| 2016/0347983 A1 * | 12/2016 | Shroff Rama | C09K 8/035 |

OTHER PUBLICATIONS

Tomac, Ingrid; "Micro-mechanical aspects of hydraulic fracture propagation and proppant flow and transport [. . . ]"; Published by Colorado School of Mines, Jan. 2007, 194 pages.*

Liang, et al.; "A comprehensive review of proppant technologies"; Petroleum vol. 2, Issue 1 (Mar. 2016), p. 26-39; <http://dx.doi.org/10.1016/j.petlm.2015.11.001>.*

* cited by examiner

*Primary Examiner* — Joseph C Rodriguez
(74) *Attorney, Agent, or Firm* — Craig W. Roddy; Tumey L.L.P.

(57) ABSTRACT

Methods to classify a proppant with respect to functional performance is described and includes measuring a coefficient of restitution for the proppant. Methods to select a proppant, methods to design a proppant, methods to predict proppant performance in a subterranean formation, and methods for providing product specifications for proppants are also described as well as other uses.

12 Claims, No Drawings

METHOD TO CLASSIFY AND SELECT PROPPANTS

BACKGROUND OF THE INVENTION

This application claims the benefit under 35 U.S.C. §119 (e) of prior U.S. Provisional Patent Application No. 61/807,518, filed Apr. 2, 2013, which is incorporated in its entirety by reference herein.

The present invention relates to proppants and the evaluation of properties of proppants. The present invention further relates to classifying proppants based on one or more properties that can be measured and further relates to methods to select proppants and design proppants based on certain properties.

In the past, to evaluate properties of proppants, metrics such as the specific gravity (sg), percent of crush fines generated at a specific pressure, sphericity, roundness, and/or actual conductivity were utilized to attempt to understand what the functional performance of a proppant may be relative to another proppant. However, while one or more of these metrics were useful in better understanding the proppant and its performance in a subterranean formation, it was discovered that these metrics alone would still not accurately predict which proppant would perform better over other proppants especially with respect to functional performance in a subterranean formation.

Accordingly, there is a need in the industry to devise additional evaluation techniques in order to better understand and predict proppant performance in subterranean formations other than the specific metrics mentioned above.

SUMMARY OF THE PRESENT INVENTION

A feature of the present invention is to provide methods to classify a proppant with respect to functional performance in a subterranean formation.

A further feature of the present invention is to provide a method to select a proppant for use in a subterranean formation from two or more types of proppants.

An additional feature of the present invention is a method to select a proppant based on a new metric that is measured for two or more proppants and then selecting based on this measured new metric.

Another feature of the present invention relates to a method for classifying a volume of proppant material into fractions on the basis of the new metric, that may include the ability of the proppant to bounce differentially within that volume.

An additional feature of the present invention is to design a proppant with respect to functional performance in a subterranean formation.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method to classify a proppant with respect to functional performance in a subterranean formation. The method comprises or includes measuring a coefficient of restitution of the proppant to obtain a measured coefficient of restitution, and then utilizing the measured coefficient of restitution to classify the proppant with respect to functional performance.

The present invention further relates to a method to select a proppant for use in a subterranean formation from two or more types of proppants. The method comprises or includes measuring a coefficient of restitution for each of the two or more types of proppants to obtain a measured coefficient of restitution for each type of proppant. The method further includes selecting a proppant at least in part based on the measured coefficient of restitution. The method can further include, as an option, a step of selecting which involves selecting the proppant with the highest measured coefficient of restitution from the two or more types of proppants.

Furthermore, the present invention relates to a method to select a proppant having a measured coefficient of restitution from two or more proppants, each having a measured coefficient of restitution. The method comprises or includes selecting based on the measured coefficient of restitution.

Also, the present invention relates to a method to design a proppant with respect to functional performance in a subterranean formation. The method comprises or includes forming a proppant so as to have a coefficient of restitution that is sufficient to provide the desired functional performance of the proppant in the particular subterranean formation. The method can comprise or include forming a proppant to have a coefficient of restitution that is greater than a coefficient of restitution for sand (e.g. sand having a 20/40 mesh).

Also, the present invention relates to a method to predict the functional performance of a proppant prior to, and/or during, and/or after its use in a subterranean formation. The method comprises or includes measuring a coefficient of restitution of the proppant to obtain a measured coefficient of restitution. The method can optionally include also utilizing the measured coefficient of restitution to compare to a library of measured coefficients of restitution for various proppants so as to determine the expected functional performance of the proppant.

The present invention also relates to methods for providing product specifications for proppants. The present invention further relates to designating, promoting, or representing grades, types, and/or brands of proppants based on coefficient of restitution values. The present invention further relates to specifying lots, batches, or shipments of proppants based on coefficient of restitution values.

Thus, the present invention also relates in part to a method for creating a product specification for a batch, lot, or shipment of proppant which involves specifying a coefficient of restitution property value for the batch, lot, or shipment of proppant. The coefficient of restitution value can be included on a product specification sheet for the brand or grade of proppant. At least one other property or value can also be specified and which may also be included on a product specification sheet.

The present invention also relates to a method of identifying or representing a grade, brand, or type of proppant by assigning or providing at least one coefficient of restitution value to the grade, brand, or type of proppant. At least one other value or property can also be assigned, such as specific gravity, crush strength, bulk density, and the like.

The present invention also relates to a method for proppant manufacturers to provide proppants to customers comprising the step of designating at least one coefficient of restitution value to a grade, brand, or type of proppant.

The present invention also relates to a method of placing an order for proppant comprising the step of placing an order for proppant by specifying at least one assigned coefficient of restitution value. The coefficient of restitution value of the proppant may be requested by the customer and/or manufacturer either prior to or at the time of placing the order.

The present invention also relates to a method for improving identification of a batch, lot, or shipment of proppant comprising a step of updating an existing specification for a batch, lot, or shipment of proppant by adding or specifying at least one coefficient of restitution value.

The present invention also relates to a method for improving identification of a grade, type, or brand of proppant, which includes the step of updating an existing description of a grade, type, or brand or proppant by indicating or representing at least one coefficient of restitution value for the grade, type, or brand of proppant.

The present invention also provides methods to prop open subterranean formation factors by utilizing proppants and the one or more methods described above and/or measuring the coefficient of restitution for the proppants.

It is to be understood that both the foregoing general description and the following detailed description are exemplary and explanatory only and intended to provide a further explanation of the present invention, as claimed.

DETAILED DESCRIPTION OF THE PRESENT INVENTION

The present invention relates to proppants and the evaluation of properties of proppants based on the coefficient of restitution for the proppant. By measuring the coefficient of restitution for a proppant or various types of proppants, this metric can be a key to fully or at least partially understanding how a proppant may perform functionally in real-world conditions. In other words, with the coefficient of restitution being known, a determination can be made, ahead of time, on how a proppant will perform in a subterranean formation when the proppant is used for fracking a well site or subterranean formation.

The coefficient of restitution (COR) is the ratio of speed of separation to speed of approach in a collision. For a single moving body $$C_R \equiv \frac{v'}{v_0},$$

where $v_0$ is the initial velocity, and $v'$ is the velocity after the bounce.

The reason that the COR can be useful and important is related to the effective transport of the proppant in a fracture through which the proppant slurry is passing. As the proppant pack begins to build in the structure, additional particles of proppant which encounter the proppant pack may do one of two things: first, the proppant particle may hit the pack and stay; or second, the proppant particle may hit the pack and rebound and be transported further into the pack. At any given velocity, the tendency of the proppant particle to rebound and be carried further into the fracture is seen as being directly related to the COR.

Testing of various types of proppant can be completed to understand if different types of proppants have different or significantly different coefficients of restitution. The testing can consist of dropping a sample of proppant of known size and Sg from a set height onto a flat surface and measuring the relative height of the rebound. The height of the rebound would correlate in air directly with the rebound velocity and provide a good relative measure of expected COR of the proppant when used in a well or subterranean formation. The COR can in fact be further characterized as the square root of the ratio of the height according to the following formula:

$$\tfrac{1}{2} mv^2 = mgh$$

where m is the mass of the particle, g is gravity, and v is the particle velocity.

The COR can be measured in a vertical drop test by measuring the drop height and the rebound height. For a drop height $h_o$ the impact velocity is given by the following formula:

$$mgh_o = \tfrac{1}{2} mv_o^2$$

where m is the mass of the particle, g is gravity, and $v_o$ is the particle velocity at impact.

The rebound height h' is given by the following formula:

$$mgh' = \tfrac{1}{2} mv'^2$$

where v' is the rebound velocity.

Therefore for a vertical drop impact:

$$COR = v'/v_o = (h'/h_o)^{1/2}.$$

When a proppant rebounds substantially better than other samples tested, the implication is that the improved ability to rebound will increase transport in the fracture. As a secondary benefit, it is anticipated that any particular proppant sample may able to be sorted by its relative tendency to rebound. When the proppant is dropped onto a slanted platform, the distance that it travels is related directly to the COR for the particular particle of proppant. Particles that have a higher COR will travel further; those with a lower COR will travel less far. In this way, the particles can be sorted by individual COR for the individual particle.

Much like a golf ball, the response of a proppant to an energetic collision can be due to the synergistic combination of a number of physical properties manifested via a typically layered structure. The reason that the COR for a certain proppants is much greater is related to its particular structure, to its material of composition, and to its method of manufacture which gives it a resilient compressible core which compresses on impact and then rebounds after the collision, along with a surface (e.g. shell) that is strong and compliant.

By measuring the coefficient of restitution or knowing the coefficient of restitution for one or more proppants, various advantages and uses can be achieved.

The present invention thus, relates in part, to a method to classify a proppant with respect to functional performance in a subterranean formation. In this method to classify a proppant, the method comprises, consists essentially of, consists of, or includes measuring a coefficient of restitution of the proppant of interest to obtain a measured coefficient of restitution. The method can further include utilizing the measured coefficient of restitution for that particular proppant in order to classify the proppant with respect to functional performance.

This method of classifying can be useful especially if a library of proppants with known coefficient of restitution is created. Then, once a proppant is measured, that particular coefficient of restitution for the proppant can assist in or permit classifying what group of proppants would this newly measured proppant fall into. For instance, if the proppant that is being tested had a coefficient of restitution that was similar or equivalent to proppants that have performed well in real-world conditions, then it would be expected that the new proppant, due to having a similar or same coefficient of restitution, would perform in the same or similar manner in real-world conditions, that is, in a well that is being fracked. In the alternative, if the proppant that is newly tested for coefficient of restitution was similar to or equivalent to proppants that perform poorly in subterranean formations, then this would be predictive of this new proppant's performance in the well if used. With the present invention, the method to classify can include, once knowing the coefficient of restitution for a proppant, whether the proppant will be an exceptional performer for functional performance, a good performer for functional performance, an average performer for functional performance, a poor performer for functional performance, or unacceptable performer for functional performance. With the present invention, a method to classify can be provided which will help researchers, proppant users, and the oil and natural gas industry in general with understanding and classifying various proppants in order to determine whether the proppant will be satisfactory for a particular fracking job and/or whether the value of the proppant is appropriate considering its classification with regard to coefficient of restitution.

With the present invention, the coefficient of restitution can be used as a new metric for gauging or grading or evaluating proppants.

With the coefficient of restitution, one proppant can be tested to obtain the COR value, or various individual proppant particles can be randomly selected from a batch of proppant and individually tested and then the coefficient of restitution property can be averaged based on the various tests. Thus, the coefficient of restitution can be based on one test, or repeated tests of the same proppant, or can be an average of coefficient of restitution results or can be a max or min coefficient of restitution or a mode of coefficient of restitution.

The present invention further relates to a method to select a proppant for use in a subterranean formation or fracking job from two or more types of proppants or from a group of different proppants. The method comprises, consists essentially of, consists of, or includes measuring a coefficient of restitution for each of the two or more types of proppants that can be chosen so as to obtain measured coefficient of restitution for each type of proppant. The method can further include selecting a proppant based at least in part on the measured coefficient of restitution for that proppant.

In the present invention, the step of selecting can comprise or involve selecting the proppant with the highest measured coefficient of restitution from the two or more types of proppants that have been tested.

The present invention further relates to a method to select a proppant having a measured coefficient of restitution from two or more proppants where each of the two or more proppants have a measured coefficient of restitution. The method can comprise, consist essentially of, consist of, or include selecting a proppant based on the measured coefficient of restitution. The measured coefficient of restitution can be the sole factor in selecting a proppant or can be one of the factors for selecting a proppant or can be an important or critical parameter for selecting a proppant. The present invention also relates to a method to design a proppant with respect to functional performance in a subterranean formation. The method can comprise, consist essentially of, consist of, or include forming or creating a proppant so as to have a coefficient of restitution that is desirable for a particular fracking job or subterranean formation. This method can include forming or creating a proppant to have a coefficient of restitution that is greater than a coefficient of restitution for, for instance, sand (20/40 mesh), for instance Ottawa 20/40 sand. For purposes of this method as well as other methods of the present invention, the coefficient of restitution for the proppant being formed or designed can preferably have a coefficient of restitution that is at least 10% greater, at least 20% greater, at least 30% greater, at least 40% greater, at least 50% greater, at least 60% greater, at least 70% greater, at least 80% greater, at least 90% greater, at least 100% greater, at least 150% greater, at least 200% greater, at least 500% greater, at least 750% greater, at least 1000% greater with respect to sand (20/40 mesh) or some other control proppant particle with a known coefficient of restitution.

The present invention also relates to a method to predict the performance of a proppant in a subterranean formation or fracking job or during a method of propping utilizing a proppant before the proppant is actually used, during the use of the proppant, and/or after the use of the proppant. The present invention would be most useful in predicting a proppant's performance prior to its use in a fracking job. However, this method can also be useful while a proppant is being used or after a proppant is being used as a further quality control check, or for other reasons.

The present invention also relates to a method of creating product specifications for batches, lots, or shipments of proppant. The present invention further relates to a method of identifying or representing a grade, brand, or type of proppant. The present invention also relates to a method of doing business with a customer which involves using a product specification. The methods of the present invention include the use of at least one coefficient of restitution value, which can be used to request a certain batch, lot, or shipment and/or to provide a certain batch, lot, or shipment of a specific grade, brand, or type of proppant. The present invention further relates to a product specification for batches, lots, or shipments of proppant that includes at least one coefficient of restitution property value. For purposes of the present invention, as used herein, the term "value" includes a specific number or value or multiple numbers or values, or a range of numbers or values.

Proppant can be made within defined specifications but even doing so it has been found that the product at times would not perform as hoped for in the customer's application (e.g., the fracking job or recovering hydrocarbons by propping with proppants). The present invention now makes it possible to specify a batch, lot, or shipment of proppant based on at least one coefficient of restitution value which enables a customer to more readily achieve the desired performance sought for when using proppants. In this way, the customer is provided with a product that should perform consistently in their end product. The present invention also provides a way to better identify or represent types, grades, and/or brands of proppant. This system permits the manufacturers and customers to better describe types, grades, and/or brands of proppant and permits those in the industry to promote more accurately the types, grades, and/or brands of proppant.

Proppant is generally made available in a variety of units, including batches, lots, samples, shipments, and the like. Typically, a customer and/or a supplier will agree on specifications for that unit of product, which may be included in a contractual agreement, including an oral agreement, purchase order, invoice, contract, waiver to a contract, or combinations thereof. A method of the present invention can involve the step of specifying at least one coefficient of restitution value to the lot, batch, sample, and/or shipment of proppant. The lot, batch, and/or shipment can be any amount, such as from small test samples to rail car size orders or larger. Furthermore, the method of the present invention may comprise the step of specifying at least one other property such as specific gravity, crush strength, bulk density, size, uniformity of size, and the like. Each, or some, of these values may be included on a product specification sheet.

The present invention further relates to a method of promoting, representing, or in some way identifying a brand, grade, or type of proppant. This method comprises naming, associating, assigning, listing, characterizing, or designating at least one coefficient of restitution value to the brand, grade, or type of proppant. At least one other property value can also be included. As used herein, representing a proppant includes any ways of identifying the material.

In view of the discoveries of the present invention, since the coefficient of restitution plays an important role for proppant performance, the method of the present invention can comprise assigning at least one property related to the coefficient of restitution property to the proppant. In this way, it has unexpectedly been found that products are better characterized and better identified, particularly to a customer. Such a specification also enables better quality assurance (QA) and quality control (QC).

The morphology of a proppant is a description of its shape, size, and structure. The morphology can include particle size, surface area, particle porosity, aggregate size, aggregate shape, maximum packing density, powder bed porosity. In addition, the morphological value can include characteristics of a distribution, such as mean, standard deviation, width, skewness, etc., of such values as particle size, pore size, aggregate size, etc. A morphological value is the result of a measurement of one of these characteristics, or combinations thereof. The surface area per unit mass, the single particle diffusion constant, the average diameter of particles, and microstructure such as the diameters, shapes, and number of pores are examples of morphological values.

The method of the present invention may further comprise the step of specifying or assigning at least one chemical value in the various embodiments of the present invention. This, along with the coefficient of restitution value and/or the morphological value may also be included on a product specification sheet. The chemistry of a proppant is the material's overall (or bulk) composition, surface composition, and/or extractable materials. The types, quantities, and arrangement of chemical moieties at the surface is called the surface chemistry.

For the method of the present invention, any proppant may be used. The proppant may be in any form. Examples of proppant include, but are not limited to, proppants that comprise, consists essentially of, consists of, or include, at least one metal, at least one metal oxide, at least one ceramic, at least one glass-ceramic, at least one polymer, at least one natural material (e.g., wood, nuts, plant material), and the like.

As described above, the coefficient of restitution value may be any property that can be correlated to the coefficient of restitution property of the proppant. For purposes of the present invention, and as described in more detail below, results from tests that can be used to determine the coefficient of restitution property, or to permit a way to assign a value to the proppant itself or to a grade or brand of proppant, which is affected by the coefficient of restitution property of a proppant are considered to be the coefficient of restitution value in the present invention. These may be determined using a variety of techniques known in the art.

Additionally, the difference in COR of individual particles of proppant within a volume of proppant may be separated into particles with high COR and particles with low COR and any fractions in between. One device that can be used to measure COR is a flat surface, such as glass, positioned horizontally or on a slant (such as a 25 degree to 45 degree slant). The amount of bounce upon hitting the flat surface (horizontal surface) and/or the distance that the proppant travels before hitting the ground (in the case of a slanted surface) can be measured per proppant tested. For instance, the proppant can be dropped from a distance of 12 inches (or 4 inches to 12 inches) high onto a glass flat surface having a thickness of ¼ inch or ⅛ inch to run this COR test. A more specific example of the test can be:

Glass surface parallel to the ground; Sample holder height: 4 inches from glass surface.

The proppant particles can be easily separated into various groups depending on the distance of bounce and roll from the initial strike point. A similar test can involve dropping the particle onto a tilted glass panel. Again, particles may be gathered into fractions based on the distance of bounce or bounce and roll. The properties of these different populations, in addition to different COR, may also be different, including the crush strength and relative sphericity of the particles.

In addition, the coefficient of restitution values may be used either alone or in combination with other values, for instance to specify a proppant itself, or to specify a batch, lot, or shipment of proppant.

For purposes of the present invention, the product specification that is related to the coefficient of restitution value can be a value specifically determined from a coefficient of restitution test, or can be a number or symbol or other denotation created to reflect, denote, or communicate a certain coefficient of restitution in a product specification. It is within the scope of the present invention to assign at least one value of a property of a proppant that is related to coefficient of restitution property, or may be either derivable from or a component of the coefficient of restitution value. Therefore, as described above, "coefficient of restitution value" can encompass the measurements of the property as well as derivations or components of any of these properties.

The present invention also relates to a product specification that includes at least one coefficient of restitution value. The product specification can also include at least one morphological and/or chemical value. The product specification can be part of a web page, a product catalog, a sales or purchase order, a contract or a waiver to a contract, and the like. The present invention provides a means to conduct business using the coefficient of restitution value(s) in product specifications for lots, samples, batches, and/or shipments. This new way of conducting business provides benefits to the overall industry as described above. Also, the present invention provides a means to represent or identify grades, types, and/or grades of proppant using at least the coefficient of restitution value(s) and to conduct business in this manner. Again, this provides numerous benefits to the industry.

The present invention also relates to a method of providing product consistency. In more detail, the present invention relates to quality control and/or quality assurance systems and methods of maintaining quality control and/or quality assurance.

A further method of the present invention involves the steps of maintaining at least one coefficient of restitution property value with a target range. As used herein, "maintaining" can include measuring or analyzing for the stated property and determining whether that value falls within the desired target ranges. If it does, the value is said to be within specifications and is therefore maintained. If it does not, in order to keep the value maintained, some change is made in the process used to prepare the proppant such that the value is brought back within range. In this way, the method of the present invention provides for product consistency by utilizing a system consisting of sampling, testing, comparison, selection, and optional process adjustment so that the product performs substantially the same.

Thus, the method of the present invention can also be considered to be a quality assurance method and/or a quality control method. Quality assurance can include the steps of sampling a product periodically, making one or more measurements on the product, comparing the results of these measurement(s) with expected or target value(s), and then releasing the product based on sufficient agreement with the expected or target value(s). Quality control can include the steps of sampling a product periodically, making one or more measurements on the product, comparing the results of these measurement(s) with expected or target value(s), transforming the measurement(s) by means of formula(e) or algorithm(s) to determine if any operation in a production process needs to be changed, changing the production process appropriately, and repeating these steps until the product meets expected value(s).

The step of maintaining at least one coefficient of restitution property value of the present invention can be done routinely, that is, they are performed as a regular part of the manufacturing process and are done prior to a customer receiving the product. Thus, the method of present invention is a quality control and/or a quality assurance method in that measurements are made periodically on the product and the results compared to target value ranges prior to a customer ever receiving the product. In more detail, one or more embodiments of the present invention relate to testing of the coefficient of restitution property in order to maintain a consistent product. Thus, one aspect of some embodiments of the present invention involves the routine testing of the proppant being made or already produced in order to insure that the product is consistent with respect to the coefficient of restitution property and optionally one or more other properties. Preferably, the routine testing of the coefficient of restitution property promotes and provides a consistent performance of the proppant in its use by a customer and its performance in the final product and any intermediate product. Routine testing can include testing for the coefficient of restitution property in proppant at regular time intervals, such as every hour or portion thereof, multiple hours, every day, every week, and the like. The routine testing can, in combination or in the alternative, be with respect to every batch or partial batch made of the proppant. The routine testing can, alternatively or in combination, include testing for the coefficient of restitution property with respect to intervals of amounts of material produced. For instance, every 1,000 pounds of the proppant produced will trigger the test for coefficient of restitution property. Needless to say, the amounts of material produced that would trigger the testing for coefficient of restitution property properties can be decided by the manufacturer or customer. Also, routine testing in the alternative or in combination can be done prior to shipping. As can be seen, from the above, routine testing generally involves testing for the coefficient of restitution property before any problem is uncovered and is done for purposes of quality control and/or quality assurance. The testing for the coefficient of restitution property to insure product performance and to insure a consistent product in the embodiments of the present invention, avoids or at least minimizes any testing triggered by a problem being uncovered, particularly by the customer. In addition, the present invention preferably provides a significant cost savings to the manufacturer and/or customer since by following a quality control and/or quality assurance system of the present invention, the amount of rejected batches of proppant should be minimized, if not completely eliminated, due to such a quality control and/or quality assurance system. Thus, this is an additional benefit of the present invention.

As part of the present invention, in one or more embodiments of the present invention, the present invention relates to a quality control system which includes a test for determining at least one coefficient of restitution property value for a proppant and also preferably a test for determining at least one other value for the same proppant. The quality control system can also include a device or medium to record at least one coefficient of restitution property value and optionally at least other value for the proppant. This recording can be done temporarily or permanently (e.g., in writing, electronically, and the like), such as on paper or with a computer program, such as Excel or any other types of software for recording data. Optionally, this data can then be compared from test to test to determine consistency. The present invention further relates to a method for quality control which includes analyzing at least one coefficient of restitution property of a proppant on a routine basis to insure quality control. Furthermore, the present invention relates to a method for quality assurance which includes analyzing at least one coefficient of restitution property of a proppant on a routine basis to insure quality assurance. The methods for quality assurance and/or quality control can further include analyzing at least one other value on a routine or non-routine basis to insure quality control and/or quality assurance.

As stated above, the method of the present invention provides product consistency by preferably maintaining both a morphological value and a coefficient of restitution property value within target ranges. The step of maintaining either value can comprise determining, measuring, or analyzing for at least one morphological value and/or coefficient of restitution property value of the proppant and adjusting at least one process variable of the process for producing the proppant. The adjustment is made so that the desired value (either the morphological value or the coefficient of restitution property value, or both) are maintained within the corresponding target range. Preferably, the adjustment is made during the process for producing the proppant. Thus, product is prepared, the properties are measured, the results are compared to the target values, and the process is accordingly adjusted, if necessary, so as to produce material having the desired property values. This is preferably done prior to the product being shipped to a customer.

A variety of different process variables can be adjusted in order to maintain the coefficient of restitution property value, such as by varying the particle size; by varying the method of particle manufacture; by varying the method of densification of the ceramic particle body; by varying the surface morphology of the proppant; by varying the spericity of the proppant particle; or by varying the amount of compressive stress in the particle.

The present invention will be further clarified by the following examples which are intended to be only exemplary in nature.

EXAMPLES

Example 1

A natural cenosphere template is fluidized and spray coated with a mixture of mixed metal oxide particles. The green body which is formed is then sintered to densify the metal oxide coating into a ceramic proppant.

Example 2

A natural cenosphere template is fluidized and spray coated with a mixture of mixed metal oxide particles. The green body which is formed is then sintered to densify the metal oxide coating. The composition of this mixed metal oxide coating has been optimized around the COR of the proppant particles.

Example 3

A natural cenosphere template is fluidized and spray coated with a mixture of mixed metal oxide particles. The green body which is formed is then sintered to densify the metal oxide coating. The composition of this mixed metal oxide coating is optimized around the COR of the proppant particles. The method of sintering is optimized around the COR of the proppant particles.

Example 4

A natural cenosphere template is fluidized and spray coated with a mixture of mixed metal oxide particles. The green body which is formed is then sintered to densify the metal oxide coating. The composition of this mixed metal oxide coating is optimized around the COR of the proppant particles. The method of sintering is optimized around the COR of the proppant particles. The particles are then sorted into different fractions according to their COR by dropping the particles onto a slanted plane or predetermined angle, composition and surface texture.

The present invention includes the following aspects/embodiments/features in any order and/or in any combination:

1. A method to classify a proppant with respect to functional performance in a subterranean formation, said method comprising measuring a coefficient of restitution of said proppant to obtain a measured coefficient of restitution, and utilizing the measured coefficient of restitution to classify the proppant.

2. A method to select a proppant for use in a subterranean formation from two or more types of proppants, said method comprising measuring a coefficient of restitution for each of the two or more types of proppants to obtain a measured coefficient of restitution for each type of proppant, and selecting a proppant at least in part based on said measured coefficient of restitution.

3. The method of any preceding or following embodiment/feature/aspect, wherein said selecting involves selecting the proppant with the highest measured coefficient of restitution from the two or more types of proppants.

4. A method to select a proppant having a measured coefficient of restitution from two or more proppants each having a measured coefficient of restitution, said method comprising selecting the proppant based on the measured coefficient of restitution.

5. The method of any preceding or following embodiment/feature/aspect, wherein said selecting involves selecting the proppant with the highest measured coefficient of restitution from the two or more proppants.

6. A method to design a proppant with respect to functional performance in a subterranean formation, comprising forming a proppant to have a coefficient of restitution that is greater than a coefficient of restitution for a control proppant having a known coefficient of restitution.

7. The method of any preceding or following embodiment/feature/aspect, wherein said control proppant is sand having a 20/40 mesh.

8. The method of any preceding or following embodiment/feature/aspect, wherein said proppant has a coefficient of restitution that is at least 10% greater than the coefficient of restitution for the control proppant.

9. The method of any preceding or following embodiment/feature/aspect, wherein said proppant has a coefficient of restitution that is at least 50% greater than the coefficient of restitution for the control proppant.

10. The method of any preceding or following embodiment/feature/aspect, wherein said proppant has a coefficient of restitution that is at least 100% greater than the coefficient of restitution for the control proppant.

11. The method of any preceding or following embodiment/feature/aspect, wherein said proppant has a coefficient of restitution that is at least 500% greater than the coefficient of restitution for the control proppant.

12. A method to predict proppant performance in a subterranean formation, comprising measuring a coefficient of restitution of said proppant to obtain a measured coefficient of restitution.

13. The method of any preceding or following embodiment/feature/aspect, wherein the measured coefficient of restitution is compared to a library of coefficient of restitution values for various proppants so as to determine proppant performance based on a comparison of the measured coefficient of restitution to the library of values.

14. A method for creating a product specification for a batch, lot, or shipment of proppant comprising specifying at least one coefficient of restitution value for said batch, lot, or shipment of proppant.

15. A method of doing business with a customer comprising using a product specification that includes a coefficient of restitution value to request a certain batch, lot, or shipment and/or to provide a certain batch, lot, or shipment of proppant.

16. The method of any preceding or following embodiment/feature/aspect, wherein the coefficient of restitution value is included on a product specification sheet, purchase order, invoice, contract, waiver to a contract, or combinations thereof for the batch, lot, or shipment of proppant.

17. The method of any preceding or following embodiment/feature/aspect, wherein said specifying comprises determining at least one coefficient of restitution value for said batch, lot, or shipment of proppant.

18. The method of any preceding or following embodiment/feature/aspect, wherein said determining comprises measuring or analyzing said batch, lot, or shipment of proppant.

19. The method of any preceding or following embodiment/feature/aspect, wherein said specifying comprises characterizing the batch, lot, or shipment of proppant by at least one coefficient of restitution property value.

20. The method of any preceding or following embodiment/feature/aspect, further comprising the step of specifying at least one morphological value to said batch, lot, or shipment of proppant.

21. The method of any preceding or following embodiment/feature/aspect, wherein the morphological value is included on a product specification sheet for the batch, lot, or shipment of proppant.

22. The method of any preceding or following embodiment/feature/aspect, wherein the morphological value is surface area, particle size, structure, porosity, or combinations thereof.

23. The method of any preceding or following embodiment/feature/aspect, further comprising the step of specifying at least one chemical value to said batch, lot, or shipment of proppant.

24. The method of any preceding or following embodiment/feature/aspect, wherein the chemical value is included on a product specification sheet for the batch, lot, or shipment of proppant.

25. The method of any preceding or following embodiment/feature/aspect, wherein the chemical value is pH.

26. The method of any preceding or following embodiment/feature/aspect, wherein the proppant is a ceramic proppant.

27. The method of any preceding or following embodiment/feature/aspect, wherein the proppant is core/shell proppant.

28. The method of any preceding or following embodiment/feature/aspect, wherein the proppant comprises at least one metal oxide.

29. The method of any preceding or following embodiment/feature/aspect, wherein the proppant comprise at least one polymer.

30. The method of any preceding or following embodiment/feature/aspect, wherein the coefficient of restitution value is determined by dropping one or more proppants on a flat hard surface and measuring height of bounce or distance travels from the first bounce, if an angled surface is used.

31. A method for representing or identifying a grade, brand, or type of proppant comprising assigning at least one coefficient of restitution value to said grade, brand, or type of proppant.

32. A method of doing business with a customer comprising requesting and/or providing a certain grade, brand, or type of proppant using an coefficient of restitution value 33. The method of any preceding or following embodiment/feature/aspect, wherein said assigning comprises determining at least one coefficient of restitution value for said grade, brand, or type of proppant.

34. The method of any preceding or following embodiment/feature/aspect, wherein said determining comprises measuring or analyzing said grade, brand, or type of proppant.

35. The method of any preceding or following embodiment/feature/aspect, wherein said assigning comprises characterizing grade, brand, or type of proppant by at least one coefficient of restitution property value.

36. The method of any preceding or following embodiment/feature/aspect, further comprising the step of assigning at least one morphological value to said grade, brand, or type of proppant.

37. The method of any preceding or following embodiment/feature/aspect, wherein the morphological value is surface area, particle size, structure, porosity, or combinations thereof.

38. The method of any preceding or following embodiment/feature/aspect, further comprising the step of specifying at least one chemical value to said grade, brand, or type of proppant.

39. The method of any preceding or following embodiment/feature/aspect, wherein the chemical value is pH.

40. A method for proppant manufacturers to provide proppant to customers comprising the step of designating at least one coefficient of restitution value to a grade, brand, or type of proppant.

41. The method of any preceding or following embodiment/feature/aspect, wherein said designation assists a manufacturer in providing a grade, brand, or type of proppant that enables a customer to achieve desired performance.

42. The method of any preceding or following embodiment/feature/aspect, wherein said designation assists a customer in obtaining a grade, brand, or type of proppant that enables the customer to achieve desired performance.

43. The method of any preceding or following embodiment/feature/aspect, further comprising the step of designating at least one morphological value to said grade, brand, or type of proppant.

44. The method of any preceding or following embodiment/feature/aspect, further comprising the step of designating at least one chemical value to said brand or grade of proppant.

45. A method of placing an order for a proppant comprising the step of placing an order for a grade, brand, or type of proppant having at least one assigned coefficient of restitution value.

46. The method of any preceding or following embodiment/feature/aspect, further comprising the step of specifying at least one coefficient of restitution value for a batch, lot, or shipment of the grade, brand, or type of proppant.

47. The method of any preceding or following embodiment/feature/aspect, further comprising the step of specifying at least one morphological value for a batch, lot, or shipment of the grade, brand, or type of proppant.

48. The method of any preceding or following embodiment/feature/aspect, further comprising the step of specifying at least one chemical value for a batch, lot, or shipment of the brand, grade, or type of proppant.

49. A method for improving identification of a grade, type, or brand of proppant comprising the step of updating an existing product description for the grade, type, or brand of proppant by adding at least one coefficient of restitution value.

50. The method of any preceding or following embodiment/feature/aspect, wherein said product description is in a catalog, web site, brochure, proppant literature, advertisement, label, or combinations thereof.

51. A product specification for grades, brands, or types of proppant comprising at least one coefficient of restitution property value.

52. The product specification of any preceding or following embodiment/feature/aspect, wherein said product specification is part of a web page.

53. The product specification of any preceding or following embodiment/feature/aspect, wherein said product specification is part of a product catalog.

54. The product specification of any preceding or following embodiment/feature/aspect, wherein said product specification is part of a sales or purchase order.

55. The product specification of any preceding or following embodiment/feature/aspect, wherein said product specification is part of a contract or a waiver to a contract.

56. The product specification of any preceding or following embodiment/feature/aspect, further comprising a morphological value, a chemical value, or both to the product specification.

57. A method for distinguishing among two or more grades, brands, or types of proppant comprising identifying coefficient of restitution values for said grades, brands, or types of proppant.

58. A method for identification of a grade, type, or brand of proppant comprising the step of creating a product description for the grade, type, or brand of proppant that includes at least one coefficient of restitution value.

59. The method of any preceding or following embodiment/feature/aspect, wherein said product description is present in a brochure, product catalog, web site, contract, advertisement, or combinations thereof.

60. A method of providing product consistency comprising the steps of:
   a) maintaining at least one coefficient of restitution property value of the proppant within a target range.

61. The method of any preceding or following embodiment/feature/aspect, further comprising the step of maintaining at least one chemical value of the proppant.

62. The method of any preceding or following embodiment/feature/aspect, wherein the chemical value is pH.

63. The method of any preceding or following embodiment/feature/aspect, wherein the step of maintaining at least one coefficient of restitution property value of a proppant comprises
   i) determining at least one coefficient of restitution value of the proppant; and
   ii) adjusting at least one process variable of a process for producing the proppant, wherein the adjustment maintains the coefficient of restitution property value within the target range.

64. The method of any preceding or following embodiment/feature/aspect, wherein the coefficient of restitution property value is determined during the process for producing the proppant.

65. The method of any preceding or following embodiment/feature/aspect, wherein the coefficient of restitution property value is determined prior to shipping the proppant to a customer.

66. A method of controlling a process for producing a proppant comprising the steps of:
   a) determining at least one morphological value of the proppant and at least one coefficient of restitution value of the proppant;
   b) comparing the morphological value and the coefficient of restitution value of the proppant to a target morphological value and a target coefficient of restitution property value; and
   c) if necessary, adjusting at least one process variable for the process.

67. The method of any preceding or following embodiment/feature/aspect, wherein the process variable is correlated to the coefficient of restitution property value.

68. A method of producing a target proppant having at least one target coefficient of restitution property value, wherein the method comprises the steps of
   a) producing a sample proppant;
   b) determining at least one coefficient of restitution property value of the sample proppant;
   c) determining the difference between the coefficient of restitution property value of the sample proppant and the target coefficient of restitution property value of the target proppant;
   d) adjusting at least one process variable of the process;
   e) repeating steps a)-d) until the difference between the coefficient of restitution property value of the sample proppant and the target coefficient of restitution property value of the target proppant is less than or equal to a target delta; and
   f) producing the target proppant having the target coefficient of restitution property value using the adjusted process variables.

69. A method for quality control comprising analyzing at least one coefficient of restitution property value of a proppant on a routine basis to insure quality control.

70. A method for quality assurance comprising analyzing at least one coefficient of restitution property value in a proppant on a routine basis prior to shipment to a customer to insure quality assurance.

71. The method of any preceding or following embodiment/feature/aspect, wherein said method further comprises analyzing at least one morphological value of said proppant on a routine or non-routine basis to insure quality control.

72. The method of any preceding or following embodiment/feature/aspect, further comprising analyzing at least one morphological value of said proppant on a routine or non-routine basis to insure quality assurance.

73. A quality control system comprising a test for determining at least one coefficient of restitution value of a proppant and a device or medium to record said at least one coefficient of restitution value of said proppant.

74. The quality control system of any preceding or following embodiment/feature/aspect, further comprising a test for determining at least one morphological value of said proppant.

75. A manufacturing facility for proppant comprising the quality control system of any preceding or following embodiment/feature/aspect.

76. A proppant manufacturing facility comprising the quality control system of any preceding or following embodiment/feature/aspect, wherein said proppant is ceramic based.

77. A quality control system for a product containing a proppant comprising the quality control system of any preceding or following embodiment/feature/aspect.

78. The method of any preceding or following embodiment/feature/aspect, wherein said analyzing is done at regular time intervals during the manufacturing of said proppant.

79. The method of any preceding or following embodiment/feature/aspect, wherein said analyzing is done on a regular basis based on amounts of proppant produced.

80. The method of any preceding or following embodiment/feature/aspect, wherein said analyzing occurs at the site where said proppant is being manufactured.

81. A method to sort a plurality of proppants for use in a subterranean formation, said method comprising measuring a coefficient of restitution of the proppants to obtain a measured coefficient of restitution for each proppant or representative ones, and utilizing the measured coefficient of restitution to sort each proppant into groups.

82. The method of any preceding or following embodiment/feature/aspect, wherein said groups comprise a high performance proppant group and a low performance proppant group, wherein the high performance proppant group has a higher measured coefficient of restitution than the low performance proppant group.

83. The method of any preceding or following embodiment/feature/aspect, wherein the plurality of proppants are from the same manufacturing batch or lot.

84. The method of any preceding or following embodiment/feature/aspect, wherein the plurality of proppants are from the same production runs.

85. The method of any preceding or following embodiment/feature/aspect, wherein the plurality of proppants are from different batches or lots.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method to classify a proppant with respect to functional performance in a subterranean formation, said method comprising:
   providing the proppant, wherein the proppant comprise a sintered metal oxide coating on a ceramic core,
   dropping the proppant on a surface; and
   sorting particles of the proppant based upon a rebound distance of the proppant.

2. A method to select a proppant for use in a subterranean formation, said method comprising:
   providing the proppant, wherein the proppant comprise a sintered metal oxide coating on a ceramic core;
   determining a coefficient of restitution for the proppant, the determining comprising dropping the proppant on a surface, measuring a rebound height, and calculating the coefficient using the rebound height;
   comparing the coefficient of restitution of the proppant to a coefficient of restitution of a control proppant; and
   selecting the proppant if the coefficient of restitution of the proppant is at least 10% greater than the coefficient of restitution of the control proppant.

3. The method of claim 1, wherein the step of dropping is performed on a horizontal surface.

4. The method of claim 1, wherein the step of dropping is performed on a surface slanted at 25 degrees to 45 degrees.

5. The method of claim 1, wherein the step of dropping is performed on a glass surface.

6. The method of claim 1, wherein the proppant comprises proppant from a single production batch.

7. The method of claim 2, wherein the step of dropping is performed on a horizontal surface.

8. The method of claim 2, wherein the step of dropping is performed on a surface slanted at 25 degrees to 45 degrees.

9. The method of claim 2, wherein the step of dropping is performed on a glass surface.

10. The method of claim 2, wherein the control proppant is 20/40 mesh Ottawa sand.

11. The method of claim 2, wherein the step of determining comprises dropping the proppant from more than one height.

12. The method of claim 2, wherein the height is from 4 inches to 12 inches.

* * * * *